(12) United States Patent
Pan et al.

(10) Patent No.: US 11,083,674 B2
(45) Date of Patent: Aug. 10, 2021

(54) ORAL CARE COMPOSITIONS

(71) Applicant: Colgate-Palmolive Company, New York, NY (US)

(72) Inventors: Guisheng Pan, Philadelphia, PA (US); Dennis Ontumi, Easton, PA (US); Lin Fei, Kendall Park, NJ (US); Suman Chopra, Monroe, NJ (US); Tatiana Brinzari, Piscataway, NJ (US); Michael Stranick, Bridgewater, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 81 days.

(21) Appl. No.: 16/204,834

(22) Filed: Nov. 29, 2018

(65) Prior Publication Data

US 2019/0159984 A1 May 30, 2019

Related U.S. Application Data

(60) Provisional application No. 62/592,874, filed on Nov. 30, 2017.

(51) Int. Cl.
*A61K 8/24* (2006.01)
*A61K 8/27* (2006.01)
*A61Q 11/00* (2006.01)
*A61K 8/20* (2006.01)

(52) U.S. Cl.
CPC .................. *A61K 8/24* (2013.01); *A61K 8/20* (2013.01); *A61K 8/27* (2013.01); *A61Q 11/00* (2013.01); *A61K 2800/28* (2013.01); *A61K 2800/42* (2013.01)

(58) Field of Classification Search
None
See application file for complete search history.

(56) References Cited

U.S. PATENT DOCUMENTS

| 2,589,272 | A | * | 3/1952 | Miller | .................... C05B 13/02 423/157.2 |
|---|---|---|---|---|---|
| 2,852,341 | A | | 9/1958 | Bell et al. | |
| 2,945,754 | A | * | 7/1960 | Hignett | .................... C05C 1/00 71/37 |
| 3,666,855 | A | * | 5/1972 | Muhler | .................... A61K 8/55 424/52 |
| 2017/0143599 | A1 | | 5/2017 | Fei et al. | |

FOREIGN PATENT DOCUMENTS

| GB | 2532283 | 5/2016 |
|---|---|---|
| WO | 2002/045512 | 6/2002 |
| WO | 2016/178747 | 11/2016 |

OTHER PUBLICATIONS

International Search Report and the Written Opinion of the International Searching Authority issued in international application PCT/US2018/063095 dated Feb. 27, 2019.

* cited by examiner

*Primary Examiner* — Nannette Holloman

(57) ABSTRACT

Compounds and methods for preparing and using the compounds are disclosed herein. The method for preparing the compounds may include contacting a metal ion or salt thereof with an alkali metal polyphosphate salt in an aqueous medium. The method may also include adding a base to increase a pH of the aqueous medium.

11 Claims, 2 Drawing Sheets

ORAL CARE COMPOSITIONS

BACKGROUND

Conventional oral care products (e.g., toothpastes, whitening gels, whitening trays, etc.) and whitening agents thereof are often utilized to whiten teeth. For example, conventional whitening toothpastes including peroxides (e.g., hydrogen peroxide) are often utilized to oxidize chromophores bound to surfaces of teeth to thereby whiten the teeth. While whitening toothpastes including peroxides have proven to be effective for whitening teeth, the peroxides are often unstable and subject to degradation or reactivity with other components of the toothpastes. For example, the peroxides in whitening toothpastes are often highly reactive to conventional abrasives, such as calcium pyrophosphate, thereby reducing the whitening efficacy of the toothpastes.

In view of the foregoing, other abrasives having relatively increased compatibility with the peroxides have been utilized in the oral care products. For example, sodium metaphosphate exhibits improved compatibility with the peroxides as compared to calcium pyrophosphate; and thus, are often incorporated in the oral care products as an abrasive. Sodium metaphosphate, however, exhibits a relatively reduced cleaning power or pellicle cleaning ratio as compared to calcium pyrophosphate.

What is needed, then, are improved abrasives or compounds thereof having improved cleaning power and compatibility with peroxides.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Embodiments of the disclosure may provide a compound prepared by contacting a metal ion or a salt thereof with an alkali metal polyphosphate salt represented by formula $(XPO_3)_n$. X may be an alkali metal and n may be an average number of from about 3 to about 10. At least one of an atomic weight or a polarizability of the metal ion may be relatively greater than the alkali metal (X) of the alkali metal polyphosphate salt.

In at least one embodiment, the alkali metal (X) of the alkali metal polyphosphate salt may be sodium or potassium.

In at least one embodiment, the alkali metal polyphosphate salt may include at least one of sodium trimetaphosphate, sodium decametaphosphate, sodium hexametaphosphate, potassium metaphosphate, sodium metaphosphate, or a mixture thereof.

In at least one embodiment, the alkali metal polyphosphate salt may include sodium metaphosphate.

In at least one embodiment, the alkali metal polyphosphate salt may only include sodium metaphosphate.

In at least one embodiment, the metal ion may be a divalent metal ion.

In at least one embodiment, the heavy metal ion may be at least one of a transition metal, a group 14 metal having an atomic weight greater than sodium or potassium, or an alkali earth metal having an atomic weight greater than sodium or potassium.

In at least one embodiment, the heavy metal ion or the salt thereof may include at least one of calcium chloride ($CaCl_2$), zinc chloride ($ZnCl_2$), stannous chloride ($SnCl_2$), or a mixture thereof.

In at least one embodiment, the heavy metal ion or the salt thereof may include calcium chloride ($CaCl_2$).

In at least one embodiment, the compound exhibits an FTIR peak at $1215\ cm^{-1}$, $1010\ cm^{-1}$, and/or $780\ cm^{-1}$.

Embodiments of the disclosure may also provide a method for preparing a compound. The method may include contacting a metal ion or a salt thereof with an alkali metal polyphosphate salt represented by formula $(XPO_3)_n$. X may be an alkali metal and n may be an average number of from about 3 to about 10. At least one of an atomic weight or a polarizability of the metal ion may be relatively greater than the alkali metal (X) of the alkali metal polyphosphate salt.

In at least one embodiment, the method may include adding a base to increase a pH of the aqueous medium.

In at least one embodiment, a weight ratio of the alkali metal polyphosphate salt to the heavy metal ion or the salt thereof may be greater than or equal to 1:1 and less than or equal to 15:1.

Embodiments of the disclosure may further provide an oral care composition including an orally acceptable vehicle, and an abrasive. The abrasive may include a compound prepared by contacting a metal ion or a salt thereof with an alkali metal polyphosphate salt represented by formula $(XPO_3)_n$. X may be an alkali metal and n may be an average number of from about 3 to about 10. At least one of an atomic weight or a polarizability of the metal ion may be relatively greater than the alkali metal (X) of the alkali metal polyphosphate salt.

Embodiments of the disclosure may also provide a method for whitening teeth or a method for preventing stains on teeth. The methods may include contacting any one of the oral care compositions disclosed herein with a surface of the teeth.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF THE DRAWINGS

The accompanying drawings, which are incorporated in and constitute a part of this specification, illustrate embodiments of the present teachings. These and/or other aspects and advantages in the embodiments of the disclosure will become apparent and more readily appreciated from the following description of the various embodiments, taken in conjunction with the accompanying drawings of which.

It should be noted that some details of the drawings have been simplified and are drawn to facilitate understanding of the present teachings rather than to maintain strict structural accuracy, detail, and scale. These drawings/figures are intended to be explanatory and not restrictive.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered a novel metaphosphate compound prepared by combining an alkali metal polyphosphate salt with a metal ion or salt thereof having an atomic weight and/or a polarizability or dipole moment relatively greater than the alkali metal of the polyphosphate salts. The present inventors have also surprisingly and unexpectedly discovered that the metaphosphate compound (e.g., calcium metaphosphate compound) may be incorporated into an oral care product or the oral care composition thereof as an abrasive. The present inventors have also surprisingly and unexpectedly discovered that oral care products or oral care compositions thereof that incorporate the metaphosphate compound (e.g., calcium metaphosphate compound) as an abrasive exhibit relatively improved/increased whitening efficacy. The present inventors have further surprisingly and unexpectedly discovered that oral care products or oral care compositions thereof that incorporate the metaphosphate compound (e.g., calcium metaphosphate compound) as an abrasive exhibit relatively improved/increased stain prevention.

Compositions disclosed herein may be or include one or more metaphosphate compounds ("modified metaphosphates") produced, formed, or otherwise prepared by mixing, combining, reacting, ion exchanging, or otherwise contacting one or more alkali metal polyphosphate salts with one or more metal ions or salts thereof ("heavy metal ions") having an atomic weight and/or a polarizability or dipole moment relatively greater than the alkali metal of the polyphosphate salts. The one or more metaphosphate compounds may be a precipitate or solid formed by mixing, combining, reacting, ion exchanging, or otherwise contacting the one or more alkali metal polyphosphate salts with the one or more heavy metal ions. As further described herein, the one or more alkali metal polyphosphate salts may be combined, reacted, or otherwise contacted with the one or more heavy metal ions in an aqueous medium to produce the one or more metaphosphate compounds.

Compositions disclosed herein may be an oral care composition including an abrasive system, where the abrasive system includes the metaphosphate compounds prepared by contacting the one or more alkali metal polyphosphate salts with the one or more heavy metal ions. Compositions disclosed herein may also be an oral care composition including an antibacterial agent, where the antibacterial agent includes the one or more metaphosphate compounds prepared by contacting one or more alkali metal polyphosphate salts with one or more heavy metal ions. The oral care composition may be a non-aqueous oral care composition, such as a non-aqueous dentifrice or toothpaste.

The oral care composition prior to use may be anhydrous. For example, the oral care composition may be free or substantially free of water. As used herein, "free of water" or "substantially free of water" may refer to a composition that contains water in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the oral care composition. The oral care composition prior to use may have a "low water content". As used herein, "low water content" may refer to a composition that contains water in an amount greater than about 5 weight % and less than about 7 weight % or less than about 10 weight %.

The oral care product or the oral care composition thereof may be a single phase oral care product or single phase oral care composition. For example, all the components of the oral care product or the oral care composition thereof may be maintained together with one another in a single phase and/or vessel. For example, the all the components of the oral care product or the oral care composition thereof may be maintained in a single phase, such as a single homogenous phase. The single homogenous may be an anhydrous formulation or an anhydrous composition.

The alkali metal polyphosphate salts may generically be referred to as "metaphosphates." The alkali metal polyphosphate salts may be soluble in aqueous mediums. The alkali metal polyphosphate salts may generally be represented by formula (1), $$(XPO_3)_n \qquad (1)$$

where 'X' is an alkali metal and 'n' is an average number from about 3 to about 10 or greater (e.g, 15, 20, 25, 40, 60, 80, 100, 150, 200). The alkali metal polyphosphate salts may be cyclic molecules (n=3-10) or polymers (n>10). The degree of polymerization may vary widely. The alkali metal polyphosphate salts may include alkali metal polyphosphate salts having varying degrees of polymerization. Illustrative alkali metal polyphosphate salts may be or include, but are not limited to, sodium trimetaphosphate, sodium decametaphosphate, sodium hexametaphosphate, potassium metaphosphate, sodium metaphosphate, and the like, and mixtures or combinations thereof. The alkali metal polyphosphate salts or metaphosphates may also be or include polyphosphates, which may be represented by formula (2), $$X_{m+2}P_mO_{3m+1} \quad (2)$$

where 'X' is an alkali metal and 'm' is an integer from 1 to 10, from 2-8, from 4 to 6, or from 4 to 5.

The heavy metal ions or salts thereof may be any suitable heavy metal ion or salt thereof capable of or configured to produce the metaphosphate compounds when reacted or otherwise contacted with the one or more alkali metal polyphosphate salts. The heavy metal ions or salts thereof may be or include any metal ion having an atomic weight and/or a polarizability or dipole moment relatively greater than the alkali metal of the polyphosphate salt. In an exemplary implementation, the alkali metal of the polyphosphate salt is sodium or potassium, and the heavy metal ion is a metal ion having a relatively greater polarizability and/or atomic weight than sodium or potassium. For example, the heavy metal ion may be or include a transition metal, a group 14 metal having an atomic weight greater than sodium or potassium (i.e., tin and lead), an alkali earth metal having an atomic weight greater than sodium or potassium (i.e., calcium), and the like, and mixtures or combinations thereof. The heavy metal ion may be monovalent or divalent. In a preferred implementation, the heavy metal ion is a divalent metal ion, such as a calcium ion, a zinc ion, a stannous ion, or the like.

In at least one implementation, the heavy metal ion is provided by a heavy metal ion salt. The heavy metal ion salt may be or include, salts of a heavy metal ion and a halogen (e.g., chloride, bromine, etc.). For example, the heavy metal ion may be provided by a chloride salt of the heavy metal ion. In a preferred implementation, the heavy metal ion may be or include calcium, zinc, and/or tin or stannous, and the heavy metal ion salt may be calcium chloride ($CaCl_2$), zinc chloride ($ZnCl_2$), and tin or stannous chloride ($SnCl_2$). In a more preferred implementation, the heavy metal ions or salts thereof includes calcium chloride.

As discussed above, the one or more alkali metal polyphosphate salts may be combined, reacted, or otherwise contacted with the one or more heavy metal ions or salts thereof in an aqueous medium to produce the one or more metaphosphate compounds. The aqueous medium may have an acidic pH, a basic or alkaline pH, or a neutral pH. For example, the one or more alkali metal polyphosphate salts may be combined with the one or more heavy metal ions or salts thereof in an aqueous medium having an acidic pH of less than 7, less than 6.5, less than 6, less than 5.5, less than 5, less than 4.5, less than 4, or less than 3.5. In another example, the one or more alkali metal polyphosphate salts may be combined with the one or more heavy metal ions or salts thereof in an aqueous medium having an alkali pH of greater than 7, greater than 7.5, greater than 8, greater than 8.5, greater than 9, or greater than 9.5. In yet another example, the one or more alkali metal polyphosphate salts may be combined with the one or more heavy metal ions or salts thereof in an aqueous medium having a neutral pH of about 6.5 to about 7.5, preferably about 7.

In exemplary implementation, the one or more alkali metal polyphosphate salts may be combined with the one or more heavy metal ions or salts thereof in an aqueous medium having a generally neutral pH. Combining the one or more alkali metal polyphosphate salts with the one or more heavy metal ions or salts thereof in an aqueous medium may reduce the pH of the aqueous medium. For example, combining the one or more alkali metal polyphosphate salts with the one or more heavy metal ions or salts thereof in an aqueous medium may generate hydrogen ions, thereby increasing the concentration of hydrogen ($H^+$) in the aqueous medium and reducing the pH thereof. Without being bound by theory, it is believed that the alkali metal polyphosphate salts may contain active hydrogen ions that are released when reacting with the heavy metal ions or salts thereof to thereby decrease the pH of the aqueous medium.

Without being bound by theory, it is believed that the reaction between the alkali metal polyphosphate salts and the heavy metal ions or salts thereof may be represented by formula (3), $$[H_xA_yPO_3]_n + zM^{2+} \leftrightarrow [M_zPO_3]_n + yA^+ + xH^+ \quad (3)$$

where A is an alkali metal such as sodium and potassium, M is a divalent heavy metal ion or a salt thereof, such as calcium, zinc, and stannous, and each of x, y, and z, is an integer from 1 to 100. As indicated in formula (3), the reaction between the alkali metal polyphosphate salts and the heavy metal ions or salts thereof may be represented by an equilibrium. Accordingly, it should be appreciated that the pH of the reaction or aqueous medium may be adjusted to drive the reaction towards the formation of the metaphosphate compounds ($[M_zPO_3]_n$). For example, a base such as sodium hydroxide or preferably potassium hydroxide may be added to the aqueous medium to increase the production of the metaphosphate compounds. Any amount of the base (e.g., potassium hydroxide) may be added. For example, the amount of the base that may be added may be any amount sufficient to provide react at least 80 weight % of the alkali metal polyphosphate salts, at least 85 weight % of the alkali metal polyphosphate salts, at least 90 weight % of the alkali metal polyphosphate salts, at least 95 weight % of the alkali metal polyphosphate salts, at least 98 weight % of the alkali metal polyphosphate salts, or greater.

The amounts of the alkali metal polyphosphate salts and the heavy metal ions or salts thereof may vary widely. In at least one implementation, a weight ratio of the alkali metal polyphosphate salts to the heavy metal ions or salts thereof may be greater than or equal to about 1:1 and less than or equal to about 15:1. For example, the weight ratio of the alkali metal polyphosphate salts to the heavy metal ions or salts thereof may be from about 1:1, about 1.5:1, about 2:1, about 2.5:1, about 3:1, about 3.5:1, about 4:1, about 4.5:1, about 5:1, about 5.5:1, about 6:1, about 6.5:1, or about 7:1 to about 8:1, about 8.5:1, about 9:1, about 9.5:1, about 10:1, about 10.5:1, about 11:1, about 11.5:1, about 12:1, about 12.5:1, about 13:1, about 13.5:1, about 14:1, about 14.5:1, or about 15:1. In another example, the weight ratio of the alkali metal polyphosphate salts to the heavy metal ions or salts thereof may be from about 1:1 to about 15:1, about 1.5:1 to about 14.5:1, about 2:1 to about 14:1, about 2.5:1 to about 13.5:1, about 3:1 to about 13:1, about 3.5:1 to about 12.5:1, about 4:1 to about 12:1, about 4.5:1 to about 11.5:1, about 5:1 to about 11:1, about 5.5:1 to about 10.5:1, about 6:1 to about 10:1, about 6.5:1 to about 9.5:1, about 7:1 to about 9:1, about 7:1 to about 8.5:1, about 7:1 to about 8:1, or about 7.5:1. In a preferred implementation, the weight ratio of the alkali metal polyphosphate salts to the heavy metal ions or salts thereof may be from about 7:1 to about 8:1 or about 7.5:1.

In another implementation, the weight ratio of the alkali metal polyphosphate salts to the heavy metal ions or salts thereof may be greater than or equal to about 20:1 and less than or equal to about 26:1. For example, the weight ratio of the alkali metal polyphosphate salts to the heavy metal ions or salts thereof may be from about 20:1, about 20.5:1, about 21:1, about 21.5:1, about 22:1, or about 22.5:1 to about 23.5:1, about 24:1, about 24.5:1, about 25:1, about 25.5:1, or about 26:1. In another example, the weight ratio of the alkali metal polyphosphate salts to the heavy metal ions or salts thereof may be from about 20:1 to about 26:1, about 20.5:1 to about 25.5:1, about 21:1 to about 25:1, about 21.5:1 to about 24.5:1, about 22:1 to about 24:1, about 22.5:1 to about 23.5:1, or about 23:1. In a preferred implementation, the weight ratio of the alkali metal polyphosphate salts to the heavy metal ions or salts thereof may be from about 22.5:1 to about 23.5:1 or about 23:1.

As discussed above, the compositions disclosed herein may be an oral care composition. The oral care composition may form at least a portion of or be used in one or more oral care products. The oral care composition may include or be combined with an orally acceptable vehicle to form the oral care product (e.g., the toothpaste). Illustrative oral care products may include, but are not limited to, a toothpaste (dentifrice), a prophylactic paste, a tooth powder, a tooth polish, a tooth gel (e.g., a whitening gel), a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the oral care composition may be or may form at least a portion of a toothpaste.

In at least one implementation, the orally acceptable vehicle may include one or more humectants. Illustrative humectants may be or include, but are not limited to, glycerin, propylene glycol, polyethylene glycol, and combinations thereof. In a preferred implementation, the orally acceptable vehicle may be or include, but is not limited to, propylene glycol. The propylene glycol may be present in an amount of from 5 weight % to about 60 weight %, based on a total weight of the oral care composition. For example, the propylene glycol may be present in an amount of from about 5 weight %, about 10 weight %, about 15 weight %, or about 20 weight % to about 25 weight %, about 30 weight %, about 35 weight %, about 40 weight %, about 45 weight %, about 50 weight %, about 55 weight %, or about 60 weight %. In another example, the propylene glycol may be present in an amount of from about 5 weight % to about 60 weight %, about 10 weight % to about 55 weight %, about 15 weight % to about 50 weight %, about 20 weight % to about 25 weight %, about 20 weight % to about 40 weight %, about 20 weight % to about 35 weight %, about 20 weight % to about 30 weight %, or about 20 weight % to about 25 weight %. In an exemplary implementation, the propylene glycol may be present in an amount of about 20 weight % to about 30 weight %, preferably about 20 weight % to about 25 weight %, and more preferably about 22 weight % to about 25 weight %. In a preferred implementation, the propylene glycol may be present in an amount of about 22 weight % to about 25 weight % or about 23 weight %.

The oral care product or the composition thereof may include one or more whitening agents. The whitening agents may be or include, but are not limited to, hydrogen peroxide or one or more sources of hydrogen peroxide. For example, the whitening agents may be hydrogen peroxide and/or hydrogen peroxide releasing substances. The one or more sources of hydrogen peroxide may be or include any compound or material configured to release hydrogen peroxide. Preferably, the whitening agents include, but are not limited to, solid whitening agents and bound whitening agents which are substantially anhydrous oxygen generating compounds. Solid whitening agents may include, but are not limited to, peroxides and persulfates. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include, but are not limited to, lithium peroxide, potassium peroxide, sodium peroxide, magnesium peroxide, calcium peroxide, barium peroxide, and mixtures thereof. Organic peroxy compounds include, but are not limited to, urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include, but are not limited to, organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. The whitening agents may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some implementations, it may be desirable to use any known whitening agent except sodium percarbonate and/or any of the percarbonate salts. The sources of hydrogen peroxide or whitening agents may also be or include, but are not limited to, PEROXYDONE™ XL 10 complex or POLYPLASDONE® XL 10F, which are commercially available from Ashland Inc. of Covington, Ky. In a typical implementation, the source of hydrogen peroxide includes a cross-linked PVP hydrogen peroxide complex.

The amount or concentration of the source of hydrogen peroxide present in the oral care product or the oral care composition thereof may vary widely. In at least one example, the source of hydrogen peroxide may be present in an amount that provides a concentration of hydrogen peroxide of less than or equal to 5 weight %, less than or equal to 4.5 weight %, less than or equal to 4 weight %, less than or equal to 3.5 weight %, less than or equal to 3 weight %, less than or equal to 2.5 weight %, less than or equal to 2 weight %, or less than or equal to 1.5 weight %, based on a total weight of the oral care product or the composition thereof. In at least one implementation, the source of hydrogen peroxide may be present in an amount greater than or equal to 1 weight % and less than or equal to 30 weight %, based on a total weight of the oral care composition. For example, the source of hydrogen peroxide may be present in an amount of from about 0.1 weight %, about 0.5 weight %, about 1 weight %, about 3 weight %, about 5 weight %, about 7 weight %, about 9 weight %, about 11 weight %, about 13 weight %, or about 15 weight % to about 17 weight %, about 19 weight %, about 21 weight %, about 23 weight %, about 25 weight %, about 27 weight %, about 29 weight %, or about 30 weight %. In another example, the source of hydrogen peroxide may be present in an amount of from about 1 weight % to about 30 weight %, about 2 weight % to about 29 weight %, about 3 weight % to about 28 weight %, about 5 weight % to about 27 weight %, about 7 weight % to about 25 weight %, about 9 weight % to about 23 weight %, about 11 weight % to about 21 weight %, about 13 weight % to about 19 weight %, or about 15 weight % to about 17 weight %. In some embodiments, the source of hydrogen peroxide is a cross-linked PVP complexed with hydrogen peroxide, and is present in an amount of from about 8 weight % to about 14 weight %, optionally about 10 weight % to about 12 weight %, and further optionally about 11 weight %. In some embodiments, the cross-linked PVP complexed with hydrogen peroxide, is present in an amount of from about 0.5 weight % to about 25 weight %, optionally about 5 weight % to about 20 weight %, or from about 7.5 weight % to about 18 weight %, or from about 9 weight % to about 17 weight %, or about 16.5 weight %.

The oral care product or the composition thereof may include an abrasive system including one or more abrasives. As used herein, the term "abrasive" may also refer to materials commonly referred to as "polishing agents". Illustrative abrasives may include, but are not limited to, metaphosphate compounds, phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate and the like, calcium carbonate, magnesium carbonate, hydrated alumina, silica, zirconium silicate, aluminum silicate including calcined aluminum silicate, polymethyl methacrylate, and the like, and mixtures or combinations thereof. In a preferred implementation, the abrasive includes the one or more metaphosphate compounds formed by contacting the one or more alkali metal polyphosphate salts with the one or more metal ions or salts thereof.

The one or more of the abrasives in the abrasive system may have a pellicle cleaning ratio (PCR) greater than or equal to 80, greater than or equal to 82, greater than or equal to 84, greater than or equal to 86, greater than or equal to 88, greater than or equal to 90, greater than or equal to 92, greater than or equal to 94, greater than or equal to 96, greater than or equal to 98, greater than or equal to 100, greater than or equal to 102, greater than or equal to 104, greater than or equal to 106, greater than or equal to 108, greater than or equal to 110, greater than or equal to 112, or greater.

In at least one implementation, the abrasive system includes a single abrasive, such as the metaphosphate compounds. In another implementation, the abrasive system includes a mixture or combination of at least two abrasives. For example, the abrasive system may include a combination or mixture of one or more metaphosphate compounds and an additional abrasive.

The amount or concentration of the abrasive system and abrasives thereof present in the oral care product or the oral care composition thereof may vary widely. In at least one implementation, the amount or concentration of the abrasives may be from greater than 0 weight % to about 40 weight %, based on a total weight of the oral care product or the composition thereof. For example, the amount of the abrasives present in the oral care composition may be from greater than 0 weight %, about 2 weight %, about 4 weight %, about 6 weight %, about 8 weight %, about 10 weight %, about 12 weight %, about 14 weight %, about 16 weight %, about 18 weight %, or about 19 weight % to about 21 weight %, about 22 weight %, about 24 weight %, about 26 weight %, about 28 weight %, about 30 weight %, about 32 weight %, about 34 weight %, about 36 weight %, about 38 weight %, or about 40 weight %. In another example, the amount of the abrasives present in the oral care composition may be from greater than 0 weight % to about 40 weight %, about 2 weight % to about 38 weight %, about 4 weight % to about 36 weight %, about 6 weight % to about 34 weight %, about 8 weight % to about 32 weight %, about 10 weight % to about 30 weight %, about 12 weight % to about 28 weight %, about 14 weight % to about 26 weight %, about 16 weight % to about 24 weight %, about 18 weight % to about 22 weight %, or about 19 weight % to about 21 weight %. In a preferred implementation, the amount of the abrasives present in the oral care composition may be from about 18 weight % to about 22 weight %, preferably about 19 weight % to about 21 weight %, or more preferably about 20 weight %, based on a total weight of the oral care product or the composition thereof.

In at least one implementation, the oral care products and/or the oral care composition thereof may be free or substantially free of fluoride (e.g., soluble fluoride salts). In another implementation, the oral care products and/or the oral care composition thereof may further include fluoride, such as one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, fluoride, stannous fluoride, sodium fluoride, potassium fluoride, sodium monofluorophosphate, fluorosilicate salts, such as sodium fluorosilicate and ammonium fluorosilicate, amine fluoride, ammonium fluoride, and combinations thereof. In a typical implementation, the fluoride ion source includes sodium monofluorophosphate. The amount of the fluoride ion source in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to provide a total of about 100 to about 20,000 ppm, about 200 to about 5,000 ppm, or about 500 to about 2,500 ppm fluoride ions.

It should be appreciated to one having ordinary skill in the art, that the oral care products and/or the oral care composition thereof may include other additional ingredients/components. For example, the oral care products and/or the oral care composition thereof may include anti-caries agents, desensitizing agents, viscosity modifiers, diluents, pH modifying agents, humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products or the oral care composition thereof may include an anticalculus agent. Generally, anticalculus agents may not be compatible with some oral care composition, however, implementations of the present disclosure may incorporate anticalculus agents and the oral care composition into a single phase oral care product. Illustrative anticalculus agents may include, but are not limited to, phosphates and polyphosphates (e.g., pyrophosphates), polyaminopropane-sulfonic acid (AMPS), hexametaphosphate salts, zinc citrate trihydrate, polypeptides, polyolefin sulfonates, polyolefin phosphates, diphosphonates. In a typical implementation, the anticalculus agents includes tetrasodium pyrophosphate (TSPP), sodium tripolyphosphate (STPP), or a combination thereof.

The oral care products or the oral care composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and the like, and combinations and mixtures thereof.

The oral care product or the compositions thereof may have a pellicle cleaning ratio (PCR) of greater than 80, greater than 82, greater than 84, greater than 86, greater than 88, greater than 90, greater than 92, greater than 94, greater than 96, greater than 98, greater than 100, greater than 102, greater than 104, greater than 106, greater than 108, greater than 110, greater than 112, greater than 114, greater than 116, greater than 118, greater than 120, greater than 122, greater than 124, greater than 126, greater than 128, or greater than 130. In a preferred implementation, the oral care product or the compositions thereof may have a pellicle cleaning ratio (PCR) of greater than 100 and less than 120, preferably greater than 105 and less than 115, more preferably greater than 105 and less than 110.

It should be appreciated that all ingredients for use in the compositions described herein are orally acceptable. As used herein, the expression "orally acceptable" may define an ingredient that is present in a composition as described in an amount and form that does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

Varying metaphosphate compounds (1)-(3) were prepared by combining sodium metaphosphate ($(NaPO_3)_n$) powder with varying heavy metal ion salts (i.e., metal chlorides) in an aqueous medium (i.e., water) under acid conditions. Particularly, sodium metaphosphate was combined with each of calcium chloride ($CaCl_2$), zinc chloride ($ZnCl_2$), and tin or stannous chloride ($SnCl_2$) in an aqueous medium. To prepare the compounds (1)-(3), each of the metal chlorides was combined with water according to Table 1, and the pH of the aqueous mixture was measured. After measuring the pH, sodium metaphosphate was added to the aqueous mixture and stirred for one hour, and the pH was measured. The amounts of each of the components utilized for preparing each of the varying metaphosphate compounds (1)-(3) and the pH of the aqueous mixture before and after combining the metal chloride with sodium metaphosphate are summarized in Table 1. After adding the sodium metaphosphate and stirring, the suspension was filtered without washing, and the filtered precipitate was dried in the oven. The filtered precipitate was then ground and the total metal content and soluble metal content was analyzed. The results of the metal content are summarized in Table 2.

TABLE 1

Metaphosphate Compounds (1)-(3)

| Ingredient | (1) Ca-MP | (2) Zn-MP | (3) Sn-MP |
|---|---|---|---|
| Water (g) | 85 | 85 | 85 |
| $(NaPO_3)_n$ (g) | 15 | 15 | 15 |
| $CaCl_2$ (g) | 2 | — | — |
| $ZnCl_2$ (g) | — | 2 | — |
| $SnCl_2$ (g) | — | — | 0.65 |
| pH (Metal Chloride + Water) | 6.013 | 6.281 | 2.882 |
| pH (Metal Chloride + Water + $(NaPO_3)_n$) | 3.184 | 2.246 | 2.311 |

TABLE 2

Total Metal Content of Metaphosphate Compounds (1)-(3)

| Ingredient | (1) Ca-MP | (2) Zn-MP | (3) Sn-MP |
|---|---|---|---|
| Soluble Metal Ions | 1.26% | 0.60% | 0.44% |
| Total Metal Content | 1.90% | 2.92% | 0.69% |
| Theoretical Total Metal Content | 3.42% | 6.21% | 1.32% |
| Total Conversion | 55.56% | 47.02% | 52.11% |

As indicated in Table 1, after the addition of the calcium chloride and the zinc chloride the pH of the aqueous mixtures decreased from about 6 to about 3 and about 2, respectively. As further indicated in Table 2, the percent conversions of the sodium phosphate to the metaphosphate compounds, Ca-MP, Zn-MP, and Sn-MP, were about 55%, about 47%, and about 52%, respectively.

Example 2

Additional metaphosphate compounds (4)-(6) were prepared by combining sodium metaphosphate ($(NaPO_3)_n$) powder with varying metal chlorides in an aqueous medium under basic conditions. Particularly, sodium metaphosphate was combined with each of calcium chloride ($CaCl_2$), zinc chloride ($ZnCl_2$), and tin or stannous chloride ($SnCl_2$) and the pH was adjusted. To prepare the metaphosphate compounds (4)-(6), each of the metal chlorides was combined with water according to Table 3. Sodium metaphosphate was then added to the aqueous mixture and stirred for one hour, and the pH was measured. After stirring, the pH was adjusted to about 7 with 45% potassium hydroxide (KOH). The amounts of each of the components utilized for preparing each of the varying metaphosphate compounds (4)-(6) and the pH of the aqueous mixture before and after combining the metal chloride with sodium metaphosphate are summarized in Table 3. After adjusting the pH to about 7, the suspension was filtered without washing, and the filtered precipitate was dried in the oven. The filtered precipitate was then ground and the total metal content and soluble metal content was analyzed. The results of the metal content are summarized in Table 4.

TABLE 3

Metaphosphate Compounds (4)-(6)

| Ingredient | (4) Ca-MP | (5) Zn-MP | (6) Sn-MP |
|---|---|---|---|
| Water (g) | 2766.4 | 87.2 | 86.19 |
| $(NaPO_3)_n$ (g) | 501.1 | 14.99 | 15.0 |
| $CaCl_2$ (g) | 64.4 | — | — |
| $ZnCl_2$ (g) | — | 1.99 | — |
| $SnCl_2$ (g) | — | — | 1.99 |
| pH (Metal Chloride + Water + $(NaPO_3)_n$) | 2.55 | 2.375 | 1.653 |

TABLE 4

Total Metal Content of Metaphosphate Compounds (4)-(6)

| Ingredient | (4) Ca-MP | (5) Zn-MP | (6) Sn-MP |
|---|---|---|---|
| Soluble Metal Ions | 0.76% | 0.76% | 1.12% |
| Total Metal Content | 3.14% | 5.60% | 4.75% |
| Theoretical Total Metal Content | 3.31% | 5.95% | 3.95% |
| Total Conversion | 94.81% | 94.06% | 62.16% |
| Total Metal Content After Washing | 1.81% | — | — |
| Soluble Metal Ions After Washing | 0.56% | — | — |

As indicated in Table 4, adjusting the pH of the aqueous mixture during the preparation of the metaphosphates resulted in increased yield. Metaphosphate compound (4) was washed and filtered in triplicate with deionized water, and the total metal content and soluble metal content was analyzed after washing. The results of the analysis after washing are summarized in Table 4. As indicated in Table 4, the amount of the soluble calcium ions remained relatively high after washing.

Example 3

Figure 1:
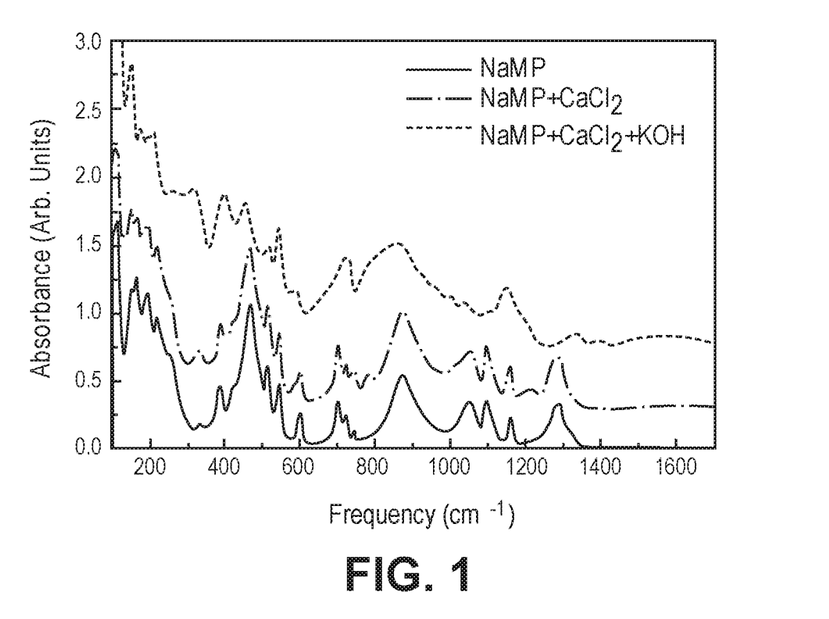
FIG. 1 illustrates the FTIR spectra of sodium metaphosphate and calcium modified metaphosphate compounds (Ca-MP) of Example 3.

The calcium modified metaphosphate compounds (Ca-MP) (1) and (4) prepared in Examples 1 and 2 were analyzed via FTIR. The FTIR spectra of the Ca-MP (1) and (4) are illustrated in FIG. 1 along with the FTIR spectra of sodium metaphosphate alone (Control). As illustrated in FIG. 1, the addition of the calcium chloride salt to sodium metaphosphate resulted in the generation of new peaks as compared to the control or sodium metaphosphate alone. For example, as illustrated in FIG. 1, new peaks were observed near 1215 $cm^{-1}$, 1010 $cm^{-1}$, and 780 $cm^{-1}$. These regions are attributed to ν(O—P—O) bridging/non-bridging and ν($PO_3$) stretching vibrations. These peaks suggest changes to the local phosphate structure upon the addition of calcium chloride. As further illustrated in FIG. 1, adjusting the pH with KOH resulted in further changes to the structure of the sodium metaphosphate. It should be appreciated that the FTIR spectra obtained for (Ca-MP) (1) and (4) were not substantially similar or equivalent to an absorption FTIR spectrum in the literature/data for any calcium metaphosphate compounds. Without being bound by theory, it is believed that one or more mixed phases may be prepared according to the methods disclosed in Example 2.

Example 4

Figure 2:
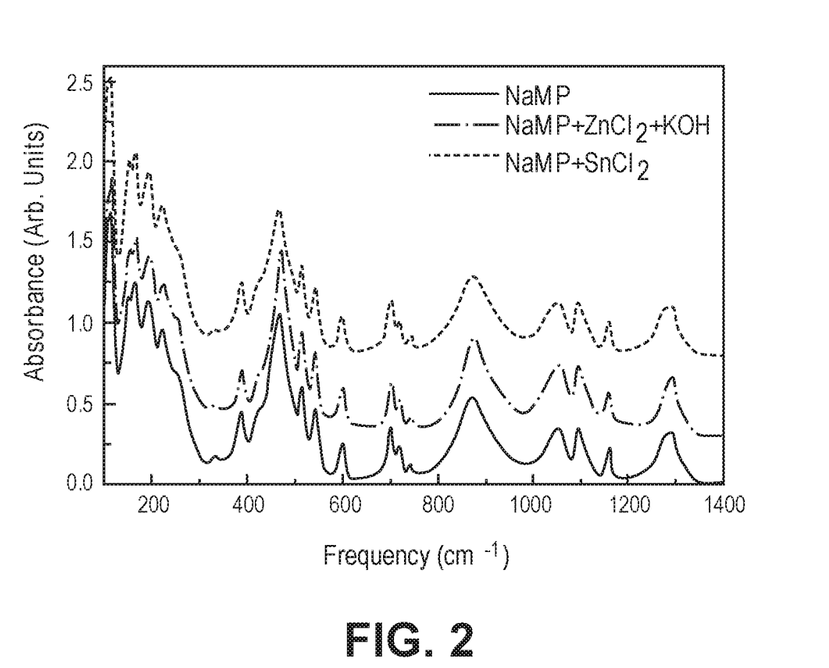
FIG. 2 illustrates the FTIR spectra of a zinc modified metaphosphate compound, a stannous/tin modified metaphosphate compound, and sodium metaphosphate of Example 4.

The zinc modified metaphosphate compound (Zn-MP) (5) prepared in Example 2 and the stannous/tin modified metaphosphate compound (Sn-MP) (3) prepared in Example 1 were analyzed via FTIR. The FTIR spectra are illustrated in FIG. 2 along with the FTIR spectra of sodium metaphosphate alone (Control). As illustrated in FIG. 2, the addition of the zinc chloride and subsequent potassium hydroxide to adjust the pH resulted in modest changes to the FTIR spectrum as compared to the Ca-MP illustrated in FIG. 1. As further illustrated in FIG. 2, the addition of the tin chloride resulted in relatively fewer changes. Particularly, the addition of the tin chloride to the sodium metaphosphate resulted in an FTIR spectrum similar to the control or sodium metaphosphate alone.

Without being bound by theory, it is believed that at least a portion of the calcium ions ($Ca^{2+}$) may weakly crosslink the metaphosphate chains of the sodium metaphosphate, and another portion or the remaining calcium ions may act as counter ions. This theory is supported by the relatively high amount of soluble calcium ions measured after washing in Example 2. It is also believed that relatively less crosslinking results from the zinc and tin ions. For example, the zinc and tin ions may serve as only counter ions in the synthesized compounds.

Example 5

The Electron Spectroscopy for Chemical Analysis (ESCA) of varying metaphosphate compounds or modified sodium metaphosphate compounds were analyzed to determine the relative surface atomic concentration and the relative ratios of carbon, phosphate, and sodium atoms thereof. The results of the ESCA analysis are summarized in Table 5 (below).

TABLE 5

ESCA Analysis of Compounds (1) and (3)-(5)

| COMPOUND | $O_{Tot}$ | Na | P | Ca Zn Sn | K | Cl | O—P | O—Na[A] | $O_{Total}$/P | Na/P | $Cation_{Total}$/P |
|---|---|---|---|---|---|---|---|---|---|---|---|
| Sodium Metaphosphate | 58.92 | 22.40 | 18.69 | — | — | — | 35.87 | 23.05 | 3.2 | 1.2 | 1.2 |
| (1) NaMP + $CaCl_2$ | 64.43 | 13.16 | 19.45 | 2.97 | — | — | 37.67 | 26.76 | 3.3 | 0.7 | 1.0 |
| (3) NaMP + $SnCl_2$ | 60.79 | 18.05 | 19.02 | 2.15 | — | — | 38.42 | 22.36 | 3.2 | 0.9 | 1.2 |
| (4) NaMP + $CaCl_2$ + KOH | 68.61 | 10.15 | 18.61 | 1.91 | 0.73 | — | 34.13 | 34.48 | 3.7 | 0.5 | 0.8 |
| (4) After Washing | 67.22 | 3.01 | 20.26 | 8.81 | 0.71 | — | 40.82 | 26.60 | 3.3 | 0.1 | 1.1 |
| (5) NaMP + $ZnCl_2$ + KOH | 56.07 | 10.60 | 15.75 | 11.54 | 3.25 | 2.8 | 42.07 | 14.00 | 3.6 | 0.7 | 2.3 |

[A]Sn, Ca, and Zn containing samples also included O bonded to these metals in addition to Na
[B]All data are averages of two analyses As indicated in Table 5, two distinct chemical states of oxygen were observed for the sodium metaphosphate; a first bonded to P in the phosphate chains and a second bonded to the Na.

For the calcium metaphosphate compound (1) NaMP+ $CaCl_2$, calcium was detected with a decrease in Na, as compared to the control (NaMP alone). The Na/P ratio for the calcium metaphosphate compound (1) was relatively lower than the sodium metaphosphate alone, indicating a loss of Na in the sample. The total cation/P ratio was also slightly lower with respect to the sodium metaphosphate alone, thereby suggesting that the amount of Ca detected was not sufficient to replace all the Na that was lost. Accordingly, it is believed that a stoichiometric ion exchange between Ca and Na has not occurred.

For tin metaphosphate compound (3) NaMP+$SnCl_2$, Sn was detected along with a decrease in Na, as compared to the sodium metaphosphate alone. The Na/P ratio for compound (3) was relatively lower than the sodium metaphosphate alone, indicating a loss of Na in the sample. The total cation/P ratio was the same as the sodium metaphosphate, thereby suggesting that the amount of Sn in the sample stoichiometrically accounts for the amount of Na lost, which is consistent with ion exchange between Sn for Na.

For calcium metaphosphate compound (4) NaMP+$CaCl_2$+KOH, both Ca and K were detected in the sample along with a decrease in Na relative to sodium metaphosphate alone. The Na/P ratio was also lower than the sodium metaphosphate alone, indicating a loss of Na. The total cation/P ratio was also relatively lower than sodium metaphosphate, which indicated that the amount of Ca and K present does not account for all the Na lost. It is believed that K replaced at least a portion of the Na. The $O_{Total}$/P ratio increased relative to sodium metaphosphate, indicating an increase in O for the sample. The ESCA does not suggest or support a stoichiometric exchange of Ca and K for Na. The increase in oxygen (O) concentration suggested that an additional compound was formed and was present. As discussed above, the identity of this compound has not been determined.

For the calcium metaphosphate compound (4) NaMP+$CaCl_2$+KOH after washing, a significantly higher concentration of Ca and lower concentration of Na was observed, as compared to before washing. The Na concentration and Na/P ratio were also substantially lower than those for sodium metaphosphate alone. The data indicates that a majority of the Na in the sodium metaphosphate was replaced by Ca, and that relatively more exchange of Ca for Na occurred as compared to before washing. A lower concentration of K was also observed, similar to before washing, which suggested that some K for Na exchange occurred. After washing, the $O_{Total}$/P ratio was similar to the sodium metaphosphate, which suggests that no additional compounds may have formed in the sample. The total cation/P ratio was slightly below that observed in sodium metaphosphate, suggesting that the amount of Ca present was not adequate to replace all of the Na lost. Without being bound by theory, it is believed that some Na was replaced by protons in the sample.

For the zinc metaphosphate compound (5) NaMP+$ZnCl_2$+KOH, high concentrations of Zn and K were observed, along with a decrease in Na relative to sodium metaphosphate. The total cation/P ratio was significantly greater than sodium metaphosphate, indicating an excess of cations present in the sample relative to the sodium metaphosphate. The $O_{total}$/P ratio was also greater than that for sodium metaphosphate, indicating an increase in O for the sample. Cl was also detected in the material. The data for this sample also did not support the stoichiometric exchange of Zn and K for Na. The excess of O and presence of Cl suggest that an additional compound(s) was present in the sample. One possible compound that could be present is a Zn hydroxy chloride, such as $Zn_5(OH)_8Cl_2$. This compound could be form when $ZnCl_2$ was combined with a strong base.

Example 6

The Ca-MP compound (4) prepared in Example 2 was evaluated for its stain removal efficacy in an oral care composition. Particularly, the Ca-MP compound (4) prepared in Example 2 was incorporated into an oral care composition (7) as an abrasive and compared with an oral care composition (8) including sodium metaphosphate as an abrasive. The oral care composition (7) including the Ca-MP compound and the oral care composition (8) (control) including sodium metaphosphate were prepared by combining the ingredients/components according to Table 6 (below).

TABLE 6

Oral Care Compositions (7) and (8)

| Ingredients | Oral Care Composition (7) | Oral Care Composition (8) |
|---|---|---|
| Phosphoric Acid | 0.1-1 | 0.1-1 |
| Polyethylene Glycol | 5-10 | 5-10 |
| Ethylene oxide/propylene oxide copolymer | 5-10 | 5-10 |
| Glycerin | 20-30 | 20-30 |
| Polyvinyl Pyrrolidone | 1-10 | 1-10 |
| Peroxide whitening agent | 0.1-20% | 0.1-20% |
| Sodium Saccharin | 0.1-1 | 0.1-1 |
| Sodium Monofluorophosphate | 0.1-2 | 0.1-2 |
| Minors (e.g. flavor, antioxidants) | 1-2 | 1-2 |
| Sodium lauryl sulfate | 2 | 2 |
| Propylene Glycol | 20-30 | 20-30 |
| Calcium Metaphosphate (Ca-MP) | 20 | — |
| Sodium Metaphosphate | — | 20 |
| Silicon Dioxide | 1-2 | 1-2 |
| TOTAL | 100 | 100 |

An in vitro brushing study of each of the oral care compositions (7) and (8) was conducted to evaluate the oral care compositions (7) and (8) for their stain removal efficacy. To evaluate the oral care compositions (7) and (8), artificial saliva was prepared, and extracted human molars were split into halves and mounted in a tray using an impression compound. The teeth were then brushed for 20 minutes with a silica toothpaste, and rinsed in 100 mL of DI water. After rinsing, each of the teeth were soaked in 25 mL of for 12 hours at 37° C. to build pellicle.

A toothpaste slurry was prepared for each of the oral care compositions (7) and (8). The toothpaste slurries were prepared by combining each of the oral care compositions (7) and (8) with artificial saliva at a 1:1 (w/w) ratio. Specifically, 12.5 g of each of the oral care compositions (7) and (8) was combined with 12.5 g of artificial saliva. The slurry was then mixed and added to each tray. Heads of manual toothbrushes were removed from their handles and mounted on a brushing assembly/machine. The teeth were brushed for a total of 2 minutes with 250 grams of pressure at a rate of 120 strokes per minute. After brushing was terminated, the slurry was removed, and residual toothpaste was rinsed away with 100 grams of deionized water. The teeth were then gently blotted with a paper towel to remove any excess liquids and measurements were taken with the hand-held spectrophotometer. The brushing treatment and measurement cycles were repeated for a total of 14 times to mimic twice daily use of each oral care composition for 7 days.

The L*, a*, b* values after treatment were compared to the baseline values to calculate the change in the whiteness of each of the teeth. The change in whiteness index (ΔW*) or whitening efficacy is summarized in Table 7. It should be appreciated that the whiteness index (W*) is a measure of overall color change relative to pure white, and is given by formula (4), and the change in whiteness index (ΔW*) is measured by formula (5).

$$W^* = ((L^* - 100)^2 + (a^*)^2 + (b^*)^2)^{1/2} \quad (4)$$

$$\Delta W^* = W^*_{treated} - W^*_{baseline} \quad (5)$$

TABLE 7

Whitening Efficacy (ΔW*) of In Vitro Brushing Treatments with Oral Care Compositions (7) and (8)

| | # of Brushing Treatments | | |
|---|---|---|---|
| | 0 | 8 | 14 |
| Oral Care Composition (7) Ca-MP (ΔW*) | 0 | −3.7 | −6.2 |
| Oral Care Composition (8) SMP/Control (ΔW*) | 0 | −1.8 | −2.0 |

As indicated in Table 7, it was surprisingly and unexpectedly discovered that the oral care composition (7) including the calcium monophosphate compound exhibited relatively greater whitening efficacy as compared to the oral care composition including the sodium metaphosphate.

Example 7

The ability of the oral care compositions (7) and (8) prepared in Example 6 were evaluated for stain prevention. To evaluate stain prevention, 24 artificially stained bovine incisors individually mounted to resin blocks were obtained from Therametric Technologies, Inc. The baseline L*, a*, b* values of the 24 mounted bovine incisors were recorded with a spectrophotometer. Whiteness index, WIO, was calculated for each sample. The enamel samples were divided into three groups with balanced mean WIO values. 8 teeth were selected for each of the oral care compositions and four teeth were mounted per tray using a thermal setting impression compound. Two trays were assigned to each product.

Heads of manual toothbrushes were removed from their handles and mounted on a brushing assembly/machine. A 3.5 g nurdle of each of the oral care compositions was added to each tray along with 7 g of artificial saliva. Brushing was immediately started, first by hand, to homogenize the nurdle, followed by the brushing machine. The teeth were brushed for a total of 2 minutes with 250 grams of pressure at a rate of 120 strokes per minute. After brushing was terminated, the slurry was removed, and residual toothpaste was rinsed away with 100 grams of deionized water.

A staining broth was prepared by filtering 900 g of a cabernet sauvignon through a fine mesh filter, steeping 9 LIPTON® tea bags in 900 g of water for 15 min, and dissolving instant coffee in 900 g of hot water. The wine, tea, and coffee were then combined with one another and stirred for 10 min to prepare the staining broth. Each of the blocks with the bovine teeth were then submerged in 10 mL of the staining broth for 20 min at 37° C. with slight agitation. After 20 min, the staining broth was removed from the tray and the bovine blocks were submerged in 10 mL of saliva for 20 min at 37° C. with agitation. The staining cycle was conduced four times for each of the bovine blocks. The results of the staining study are summarized in Table 8.

TABLE 8

Whitening Efficacy (ΔW*) for Stain Prevention of Oral Care Compositions (7) and (8)

| | (ΔW*) |
|---|---|
| Oral Care Composition (7) Ca-MP | 3.72 |
| Oral Care Composition (8) SMP/Control | 6.72 |

It should be appreciated that a lower ΔW indicates improved stain prevention. As indicated in Table 7, it was surprisingly and unexpectedly discovered that the oral care composition (7) including the prepared Ca-MP of Example 2 exhibited relatively greater stain prevention as compared to the oral care composition (8) including sodium metaphosphate.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

Example 8

Figure 3:
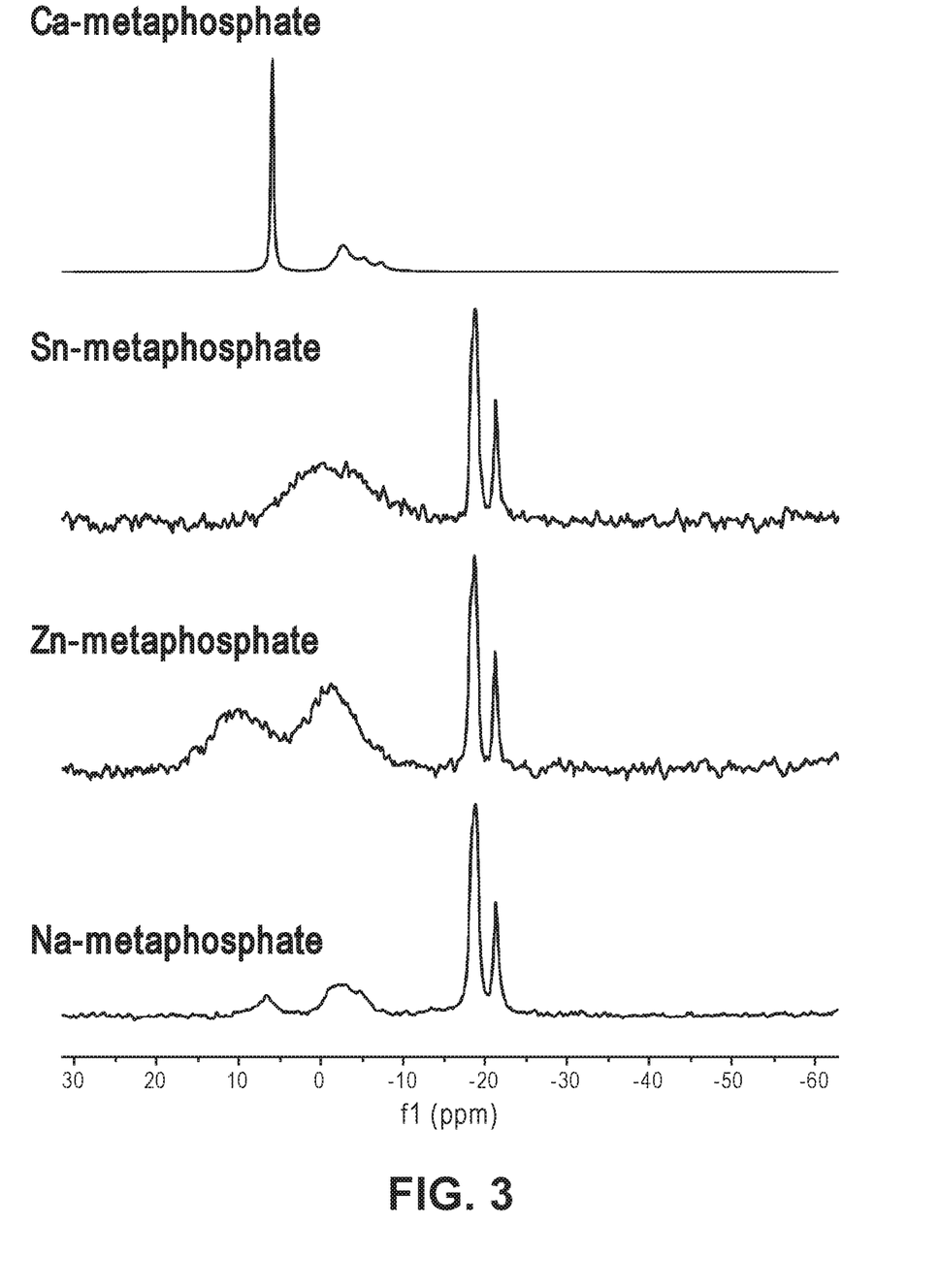
FIG. 3 illustrates 31P magic angle spinning (MAS) NMR spectrum of a calcium metaphosphate, tin or stannous metaphosphate, and zinc metaphosphate sample as prepared in Example 8, as well as a commercially-available sodium metaphosphate.

The Ca-MP (4) prepared in Example 2, as well as the Zn-MP (5) and Sn-MP (6) prepared in Example 2, were washed three times in deionized water, filtered, and dried. The samples were then analyzed via 31P MAS NMR. The NMR spectrum of the Ca-MP (4), Zn-MP (5), and Sn-MP (6) are illustrated in FIG. 3, along with the NMR spectra of sodium metaphosphate alone as a control. As illustrated in FIG. 3, the addition of the calcium chloride salt to sodium metaphosphate resulted in the generation of new peaks in the resulting Ca-MP (4) as compared to the control or sodium metaphosphate alone, indicating the formation of a new material. Likewise, the NMR spectrum for Zn-MP (5) and Sn-MP (6) confirm that the addition of zinc chloride salt and tin or stannous chloride salt, respectively, to sodium metaphosphate resulted in different materials from the starting material of sodium metaphosphate.

What is claimed is:

1. A compound prepared by contacting a metal ion or a salt thereof with an alkali metal polyphosphate salt represented by formula (1)

$$(XPO_3)_n \quad (1),$$

wherein X is an alkali metal and n is an average number of from about 3 to about 10, and wherein at least one of an atomic weight or a polarizability of the metal ion is relatively greater than the alkali metal (X) of the alkali metal polyphosphate salt, and wherein the compound exhibits an FTIR peak at 1215 $cm^{-1}$, 1010 $cm^{-1}$, and/or 780 $cm^{-1}$.

2. The compound of claim 1, wherein the alkali metal (X) of the alkali metal polyphosphate salt is sodium or potassium.

3. The compound of claim 1, wherein the alkali metal polyphosphate salt comprises sodium metaphosphate.

4. The compound of claim 1, wherein the alkali metal polyphosphate salt consists of sodium metaphosphate.

5. The compound of claim 1, wherein the heavy metal ion or the salt thereof comprises calcium chloride ($CaCl_2$).

6. A method for preparing the compound of claim 1, comprising contacting the metal ion or the salt thereof with the alkali metal polyphosphate salt in an aqueous medium.

7. The method of claim 6, further comprising adding a base to increase a pH of the aqueous medium.

8. The method of claim 6, wherein a weight ratio of the alkali metal polyphosphate salt to the heavy metal ion or the salt thereof is greater than or equal to 1:1 and less than or equal to 15:1.

9. An oral care composition, comprising:
an orally acceptable vehicle; and
an abrasive, wherein the abrasive comprises the compound of claim 1.

10. A method for whitening teeth, comprising contacting the oral care composition of claim 8 with a surface of the teeth.

11. A method for preventing stains on teeth, comprising contacting the oral care composition of claim 8 with a surface of the teeth.

* * * * *